(12) United States Patent
Solberg et al.

(10) Patent No.: US 7,950,980 B2
(45) Date of Patent: May 31, 2011

(54) SYSTEM AND DEVICE FOR SUPPORTING A BREAST SHIELD

(75) Inventors: Jill Solberg, Woodstock, IL (US); Mark Luzbetak, Kildeer, IL (US); Erich Pfenniger, Ebikon (CH)

(73) Assignee: Medela Holding AG, Baar (CH)

( * ) Notice: Subject to any disclaimer, the term of this patent is extended or adjusted under 35 U.S.C. 154(b) by 922 days.

(21) Appl. No.: 11/583,292

(22) Filed: Oct. 19, 2006

(65) Prior Publication Data

US 2008/0146118 A1    Jun. 19, 2008

(51) Int. Cl.
*A41C 3/00*    (2006.01)
(52) U.S. Cl. ............................. 450/36; 604/72; 604/73
(58) Field of Classification Search ............... 450/1, 36, 450/37, 58; 2/104; 604/72–76, 343
See application file for complete search history.

(56) References Cited

U.S. PATENT DOCUMENTS

| | | | | |
|---|---|---|---|---|
| 949,414 A * | 2/1910 | Cunningham | ................. | 604/76 |
| 1,094,158 A * | 4/1914 | Mattson | ....................... | 604/388 |
| 2,808,830 A * | 10/1957 | Perry | ............................ | 604/343 |
| 2,914,068 A * | 11/1959 | Schacht | ....................... | 604/341 |
| 3,513,852 A * | 5/1970 | Seidl | .............................. | 450/36 |
| 3,856,011 A * | 12/1974 | Blanchard | .................... | 604/343 |
| 5,571,084 A * | 11/1996 | Palmer | ........................... | 604/74 |
| 5,575,768 A | 11/1996 | Lockridge et al. | | |
| 6,004,186 A * | 12/1999 | Penny | ............................ | 450/36 |
| 6,027,396 A * | 2/2000 | Yonchar | ......................... | 450/36 |
| 6,247,996 B1 * | 6/2001 | Fields | ............................ | 450/36 |
| 6,379,327 B2 | 4/2002 | Lundy | | |
| 7,611,399 B2 * | 11/2009 | Brigham | ........................ | 450/36 |
| 2006/0211336 A1 * | 9/2006 | Brigham | ........................ | 450/86 |

* cited by examiner

*Primary Examiner* — Gloria Hale
(74) *Attorney, Agent, or Firm* — McDonnell Boehnen Hulbert & Berghoff LLP

(57) ABSTRACT

A breast shield support is provided which in one embodiment includes a central harness body adapted to hold a breast shield. The central harness body may include three spaced straps connected to or extending from the central harness body. Each of the harness straps includes a clip, for example, for attaching a respective strap to a portion of a nursing brassiere and at least one strap includes a plurality of protrusions or grooves formed along the length of the strap for engaging a respective clip and permitting the clip to be easily adjusted and held in a desired position along the length of the strap.

35 Claims, 8 Drawing Sheets

SYSTEM AND DEVICE FOR SUPPORTING A BREAST SHIELD

FIELD OF THE INVENTION

The present invention is directed to devices and systems related to use of a breast pump. In particular, the present invention provides for hands-free breast pumping. More particularly, the present invention relates to devices and systems which permit use of a breast pump in a hands-free manner, i.e., the mother need not support the breast pump with her hand. In one example, the present invention includes a breast shield harness which functions to hold a breast shield of a breast pump to a nursing garment or brassiere securely in place while breast pumping. In another example, the present invention is a hands-free pumping system including a nursing garment and a breast shield harness connectable to the nursing garment.

BACKGROUND OF THE INVENTION

At one time, a majority of mothers nourished their newborn infants by breast-feeding, but over the years, the practice of feeding infants with formula has become more commonplace. However, medical doctors and health experts are increasingly aware of the fact there are many advantages to using breast milk. This is due, at least in part because infant formula is not sophisticated enough to supplant the benefits of breast milk and further, because the content of breast milk tends to change based on the infant's nutritional needs. There is also increasing support for encouraging the use of breast milk for its immunological benefits. For at least these reasons, increasing numbers of women are once again turning to the practice of breast-feeding their children.

A woman who is nursing an infant typically will express breast milk to store for times when she is unable or unavailable to breast feed her infants. A woman may express her milk by using an electric or a manual pumping device, known in the art as a breast pump, in conjunction with a funnel, known as a breast shield. Typically, the woman holds the breast shield tightly against her breast and nipple to apply suction generated by the breast pump thereto and to direct the flow of milk into a storage container.

Often, because of the length of time required to express and collect breast milk, a woman may desire to express both breasts simultaneously. To extract milk from both breasts at the same time, the woman must typically hold a funnel with each hand against her breasts, leaving her in an awkward position, and unable to do anything else with her hands.

In the past, brassieres for breast-feeding are typically made so as to allow a nursing infant access to the woman's breast. A typical example of this type of brassiere is disclosed in U.S. Pat. No. 2,501,860, which shows a brassiere with cups that allow an infant access to the woman's breasts by means of a flap that may be folded back from a fastened condition covering the breasts.

While prior-art nursing brassieres allow an infant access to a woman's breast, they are most often not constructed to also receive and support a funnel and an associated milk container (bottle) attached to a breast pump to allow a woman to express breast milk. Those nursing brassieres that are designed for supporting a breast pump generally utilize custom brassiere features to attach to a proprietary hands-free device, which limits the user to a specific brassiere manufacture or model sometimes in combination with a matching hands-free device adapted for that brassiere. Because of the complexity of setup and adjustment and the number of components involved the marketplace has not widely accepted some of these devices.

For at least the foregoing reasons, there is a need for a device designed to allow fast, easy and secure attachment, and adjustment, of a breast shield funnel and further related breast pump apparatus to a nursing bra for expressing milk.

SUMMARY OF THE INVENTION

The present invention offers improvements in ease of attachment and also adjustability of hands-free breast pumping arrangements, and more specifically to an improved device for receiving and supporting a breast pump funnel and more on a nursing brassiere or similar garment for the purpose of expressing breast milk. The invention may be used in combination with a range of nursing brassieres that are commonly available in the market.

It is a principal object of the invention to provide a device that supports a breast shield of a breast pump upon an exposed breast in a "hands-free" manner for the user. The invention in its broadest sense contemplates a device that minimizes the complexities and adjustment problems of the prior art, as well as the often narrow range of application of certain prior art devices, whereby breast shields of many kinds can be held in position on the breast without the need of the user to hold it in place or the use of a garment specially adapted for the invention.

Breast pumps, both using manual and motor-driven pressure sources (generally vacuum) are well known. Both types of breast pumps typically share some elements, such as a portion which contacts and fits to the breast of the user. This portion is known as a breast shield and includes an open end, which in one example includes a tapered, funnel shaped (conical) portion that is sized and shaped to encompass the breast centered on the nipple. Downstream from the funnel end is a narrower generally cylindrical end, sometimes referred to as a nipple tunnel that is sized and shaped to receive the nipple of the breast and connect to a vacuum (negative pressure) pump, either directly or via a length of hosing, for example. It is envisioned that other breast shields may not include such a nipple tunnel or may have a more compressed profile and therefore may be less conspicuous. The particulars of the pumping mechanism are incidental to this invention.

In particular, the breast shield harness according to some embodiments of the invention includes a central harness body that has an opening formed therethrough. The opening is sized and shaped to receive a breast shield nipple tunnel and hold the shield in place. The harness body may otherwise be an uninterrupted panel.

The central harness body includes, in one embodiment, three spaced straps connected to or extending from the central harness body. Each of the harness straps preferably includes a clip for attaching a respective strap to a portion of a nursing brassiere as will be detailed below and a plurality of engaging elements, like channels, protrusions or teeth formed along a length of the strap for engaging a respective clip and permitting the clip to be easily adjusted and held in a desired position along the length of the strap.

One of the harness straps extends from a top edge of the central harness body and includes an upper clip for attaching to a mounting element on the nursing bra. A second and a third harness strap extends from lower parts, such as the corners, of the harness body. Each of the second and third harness straps in this embodiment includes a clip for attaching to a lower edge of a garment, such as a nursing bra, i.e., a bottom band or under wire thereof or part of the garment fabric. Nursing bra is used herein to refer to any type of such garment.

As can be seen, a three-way somewhat triangular attachment arrangement results. The upper clip, in an embodiment is adapted to attach to a stud or post or flap attachment device on the nursing bra. The lower clips, in this embodiment are adapted to attach to a lower edge or portion of the nursing bra. The upper clip may include a loop and tab, which function to ubiquitously fasten to multiple bra hardware elements currently on the market. A release tab on the upper clip permits adjustment of the strap by gripping in a first position and releasing in a second position. The clip may include a ratchet device, permitting easy tightening of the strap while preventing unwanted loosening. The invention may include the provision of a kit with other types of bra hardware clips as an add-on feature, or provide interchangeability via a universal clip.

The breast shield harness may be a molded silicone accessory that attaches to or is otherwise simply received on the breast shield to hold the breast shield against the breast for hands-free use as detailed above. The breast shield harness can include adjustable height mechanisms for both the upper (first) connection point as well as optional adjustable bottom (second and third) attachment points.

Generally, the present invention includes embodiments which are both attachable to many kinds of nursing bras, or may include its own nursing brassiere for supporting the breasts of a wearer and for receiving and supporting a funnel for expressing breast milk. The foregoing brassiere is provided with at least one cup with an opening in the center that easily accommodates a funnel to be inserted therethrough. The brassiere is comprised of a pair of cups dimensioned to substantially cover a woman's breasts. The cups have an upper edge and an arcuate or curved edge depending therefrom. A connecting portion joins the cups (between the breasts) at the inside of the curved edges of the cups. A back support is connected to the outer edge of the curved edges of the cups. Both cups preferably, include at least two interior portions that are each attached to the cup along the curved edge which form the breast cup proper. These portions are positioned such that they are not attached at their common border, so they can be separated in use. Elastic bands are attached to each of the two portions along their common border.

A breast shield funnel may be selectively inserted between and under the first and second portions of the cups and positioned so as to contact a woman's breast for creating suction by means of a pump to express milk. With the breast shield inserted, the breast shield harness holds the breast shield to provide a snug and secure fit and support the breast shield in its breast-contacting position. With the funnel or a pair of funnels firmly in place, the wearer may now contentedly express milk in a hands-free manner.

Accordingly, the embodiments of the present invention provide an improved device for use in hand free expression of breast milk. The invention frees a woman's hands to do other activities while she expresses breast milk, by supporting a funnel that creates suction and directs the flow of milk into a storage container. Still other objects and advantages of the invention will be made apparent from the specification herein. Moreover, the most preferred embodiments are readily useful over a range of different nursing bras or the like.

BRIEF DESCRIPTION OF THE DRAWINGS

While the claims concluding the specification particularly point out and distinctly claim the precise subject matter regarded as the sum and substance of the present invention, its construction and composition may be best understood from the following detailed description taken in connection with the accompanying drawings, in which:

DETAILED DESCRIPTION OF A PRESENTLY PREFERRED EMBODIMENT

Figure 1:
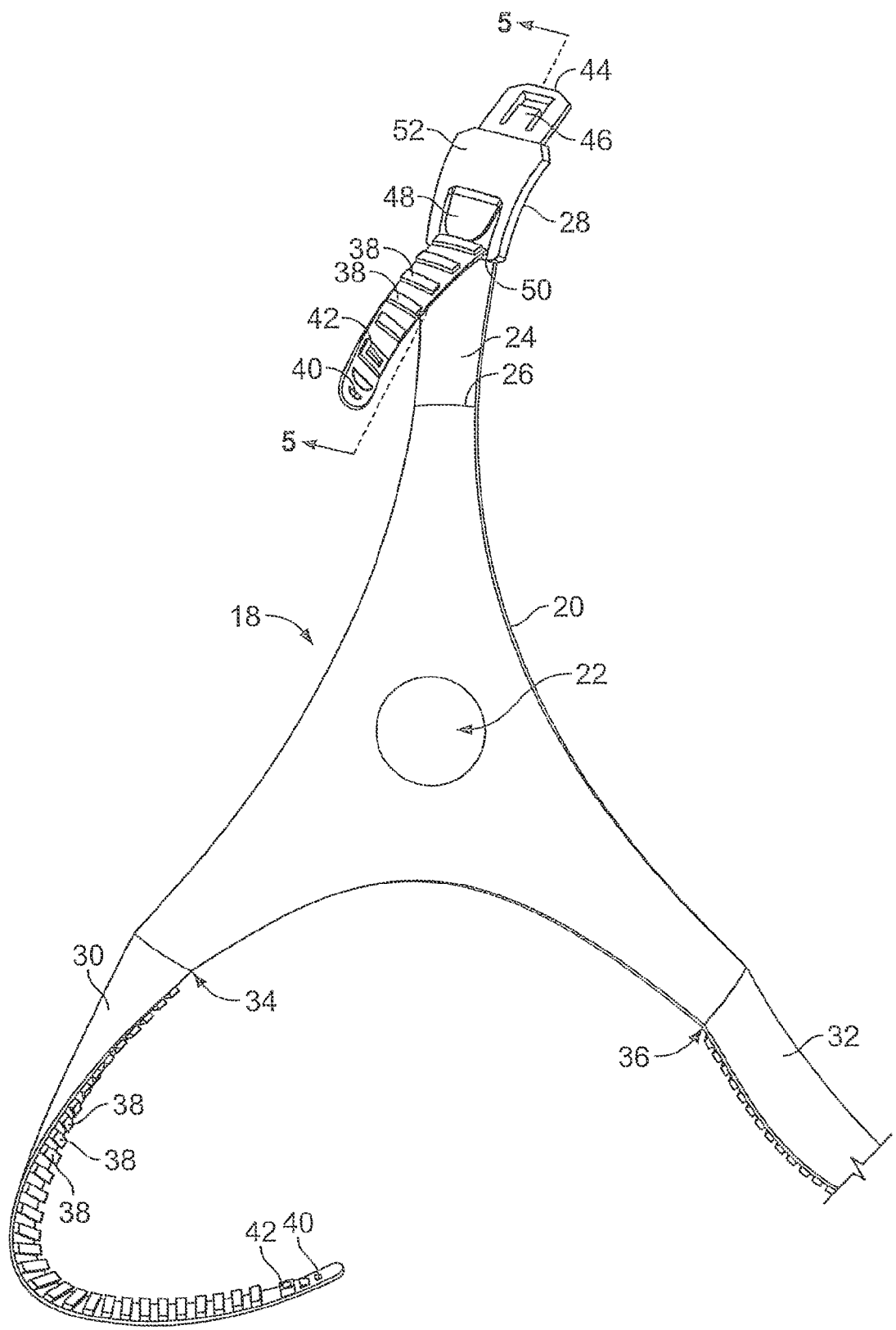
FIG. 1 shows a harness device according to one embodiment of the invention.

Referring to FIG. 1, a breast shield harness 18 is shown according to a first preferred embodiment. The breast shield harness 18 includes a central harness body 20, with a body opening 22 defined therein that is sized and shaped to receive and hold is a breast shield (see FIG. 2) in place.

The central harness body 20 has a top portion indicated at 26 from which a first strap 24 extends. Similarly, the central harness body 20 includes a first lower portion at upper transition 34 from a "corner" and a second lower portion at transition 36, for another "corner." The top edge 22, first and second transitions 34, 36 are positioned to roughly define a triangular shape of the central harness body 20. It will be understood that other suitable shapes are contemplated by the invention. These transitional areas or "corners" are also set forth merely for orientation of the reader and have no significant structure or functional meaning.

A second strap 30 extends from the first lower corner 34 and a third strap 32 extends from the second lower corner 36. In a preferred embodiment, the straps 24, 30 and 32 and the harness body 20 are formed of a silicone rubber material, which provides a nice grip and also some stretchability. Other materials may readily be used, however. The straps 24, 30 and 32 may be formed in a unitary fashion with the harness body 20 or may be attached thereto by any suitable method, for example, use of heat or an adhesive, and may be of a material different from the body 20.

Each of the straps 24, 30 and 32 all include, along their length, a plurality of protrusions or teeth 38, which also may be considered to define grooves, therebetween. The protrusions 38 permit each the straps to be individually fixed in position with respect to a clip body, one of which is found at first clip 28. The end of each strap 24, 30 and 32 may include one or more finger-gripping elements 40 which are bumps, protrusions, teeth, ramps or a saw tooth shaped feature for the user to grip. Between the protrusions 38 and the gripping elements 40 is a stop element 42, which is a protrusion larger than protrusions 38 and is shaped and sized to not easily pass through a clip on the strap. In this manner, clips, for example first clip 28 cannot be easily detached from the strap 24 by merely sliding off the end of the strap because the stop element 42 does not pass through the associated clip, described hereafter.

Figure 3:
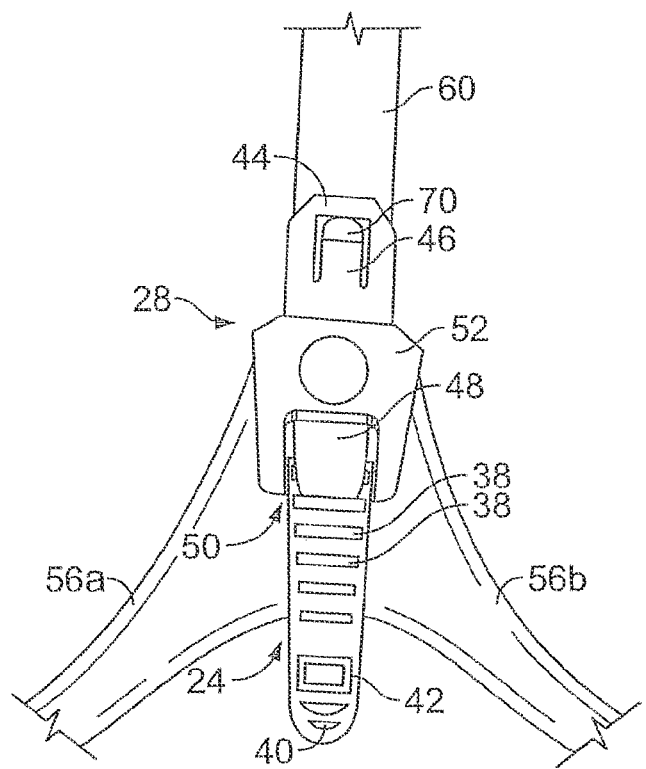
FIG. 3 shows a close up view of the breast shield harness device of FIG. 1 fastened to a nursing bra.

The first clip 28, shown attached to the first strap 24 includes a clip body 52 with a lower (relative to the user) passageway 50 formed therethrough. The lower passageway 50 is sized and shaped to receive the first strap 24. A release tab 48, when in a first position, traps the strap 24 in place and when in a second position, permits the strap 24 to be slid through the clip body 52 and adjusted thereby. At an end opposite the passageway 50 is a loop 44 and tab 46, which is designed to receive a fastener of a nursing brassiere, which will be shown in more detail in FIG. 3.

The clip body 52 has a passageway 50 formed therethrough at an end opposite the loop 44, which passageway is sized and shaped to receive strap 24. A tab 48 is biased to close the passageway 50 and hold the strap 24 in place by engaging protrusions 38 of the strap or pressing the protrusions against the clip body 52 so as to prohibit the strap from slipping through the passageway. A stop feature 42 may be formed near the end of the strap 24 to prohibit the strap from slipping through the passageway 50 when the tab 48 is lifted and disengaged from the strap. Ridges or similar engaging features 40 may be formed near the end of the strap 24 to provide an enhanced grip on the strap. The foregoing clip device 28 is very much like that used with a diving mask.

Figure 2:
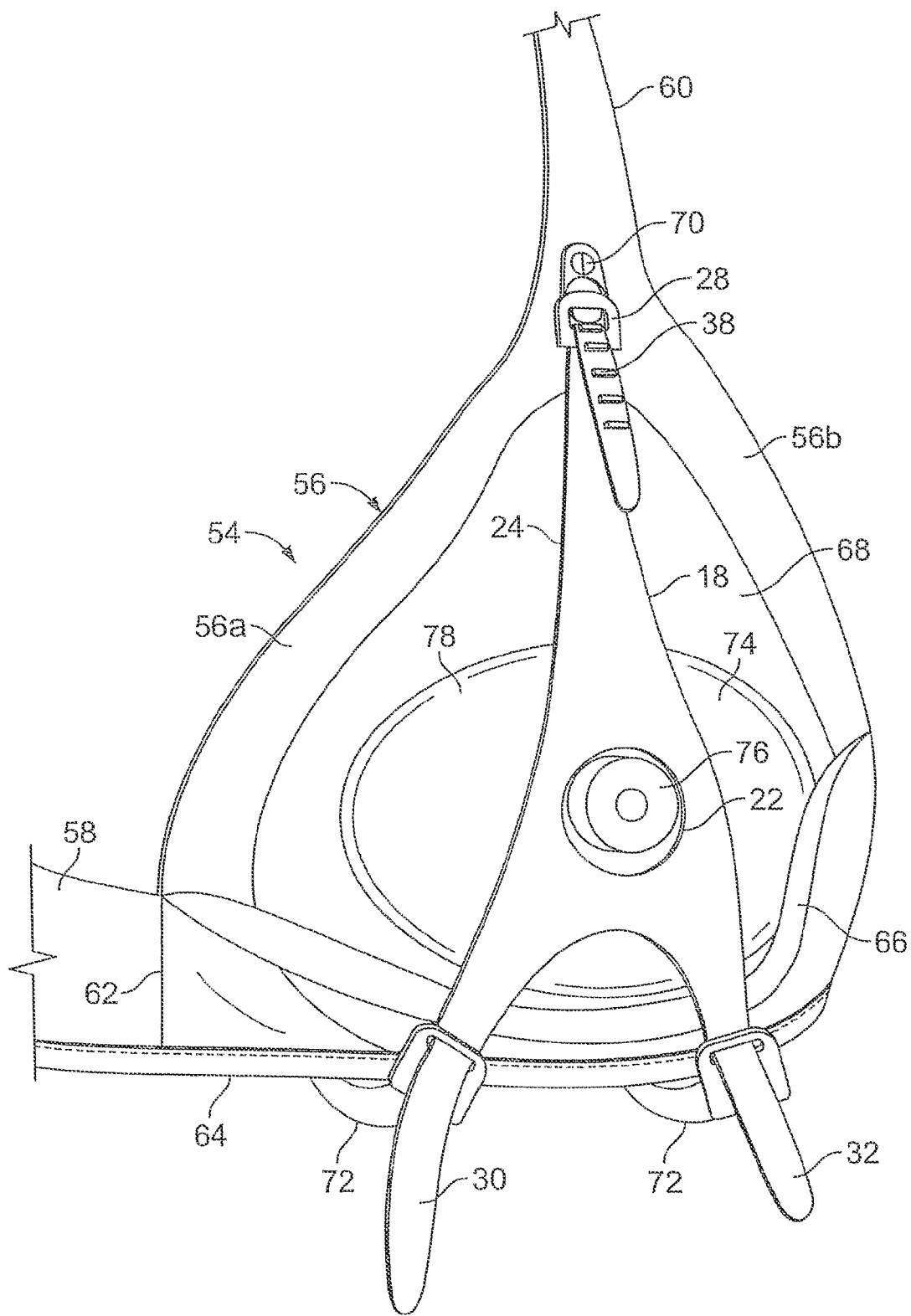
FIG. 2 shows the harness device of FIG. 1 in use with a breast shield and a nursing bra.

Referring now to FIG. 2, a brassiere, generally indicated at 54, is shown in a partial view. The depicted partial portion of a brassiere 54 includes a first cup 56, a connector portion 58, and a shoulder strap 60. Connector portion 58 is connected or sewn to an inner edge 62 of first cup 56. Connector portion 58 may be made of a flexible and/or elastic material, such as Spandex®, lace, or loosely knit cotton, for a few examples.

The shoulder strap 60 extends and divides into a first wing 56a and a second wing 56b of cup 56. First wing 56a connects to a bottom band 64 of the brassiere 54, which may include a wire, as is known in the art, for support. Similarly, the second wing 56b connects to the bottom band 64 to generally define the cup 56 with the first wing 56a and the bottom band 64 and the cup opening 68, which permits access to the underlying breast.

The brassiere 54 includes a flap 66, which covers the cup opening 68 in a first position and permits access to the breast through the cup opening when in a second position as presently depicted. The brassiere 54 also includes a post 70 designed for fastening the flap 66 in the first position, i.e., a breast-covering position. Clip 28 attaches to the post 70.

A breast shield 74 is shown positioned in the cup opening 68. The funnel shaped portion 78 is positioned in contact with the breast of the user and the cylindrical portion 76 is inserted through the harness body opening 22 with the central harness body 20 overlying the breast shield 74. Opening 22 may be sized to accommodate a wide variety of conventional breast shields, or may be elastically expandable to accomplish the same versatility.

The post 70, which is a conventional flap fastener for nursing brassieres, is also used to fasten the first clip 28 of the breast shield harness 18. The clip 28 is fastened to the post 70 and the second and third straps 30, 32 are connected to the bottom band 64 by attaching lower clips 72 thereto. The straps 24, 30 and 32 may be adjusted and are held in place by protrusions 38 engaged with the clips 28, 72.

The rest of breast pump assembly (not shown) may be attached to the breast shield portion 76 as is conventionally done and thus, breast pumping may proceed in a manner not requiring use of other means to hold the breast shield to the breast, i.e., in a hands-free manner.

While only one side (one cup) of the brassiere 54 is shown, it will be understood that the brassiere typically has two cups and associated elements, and therefore the other cup would be the same as previously described with another harness for holding respective breast shields. Thus, the user can express twice the milk in about the same amount of time, while still having her hands free to do other things. Of course, brassieres may be constructed such that only one cup is constructed to accept a funnel.

Figure 3A:
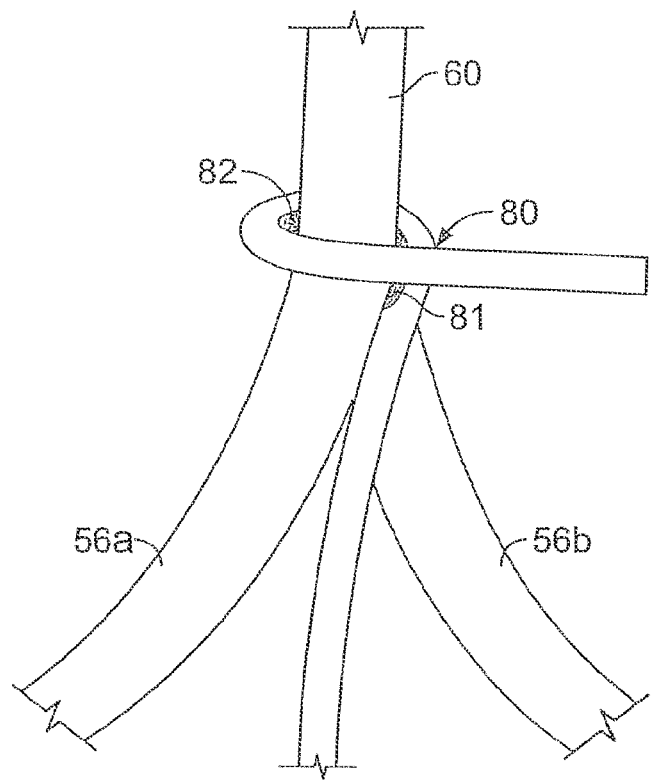
FIG. 3A is a modified version of the embodiment of FIG. 3, using a hook and loop type fastener for the upper attachment.

Turning to FIG. 3a, another example of a fastening device for connecting to a shoulder strap 60 of a brassiere or like garment is shown. The fastener 80, in this case is a hook and loop (VELCRO™) fastening device having the hook material on one side and the loop material on the other, e.g., including respective areas 81, 82. The user simply wraps the fastener around the strap 60 at a point which may be above first and second wings 56a, 56b of the garment, with a twist, to then affix the hook and loop material where overlapped. Other fastening arrangements that attach to themselves to form a fastening loop are well known (e.g., a toggle adjustable-type clip).

Figure 4:
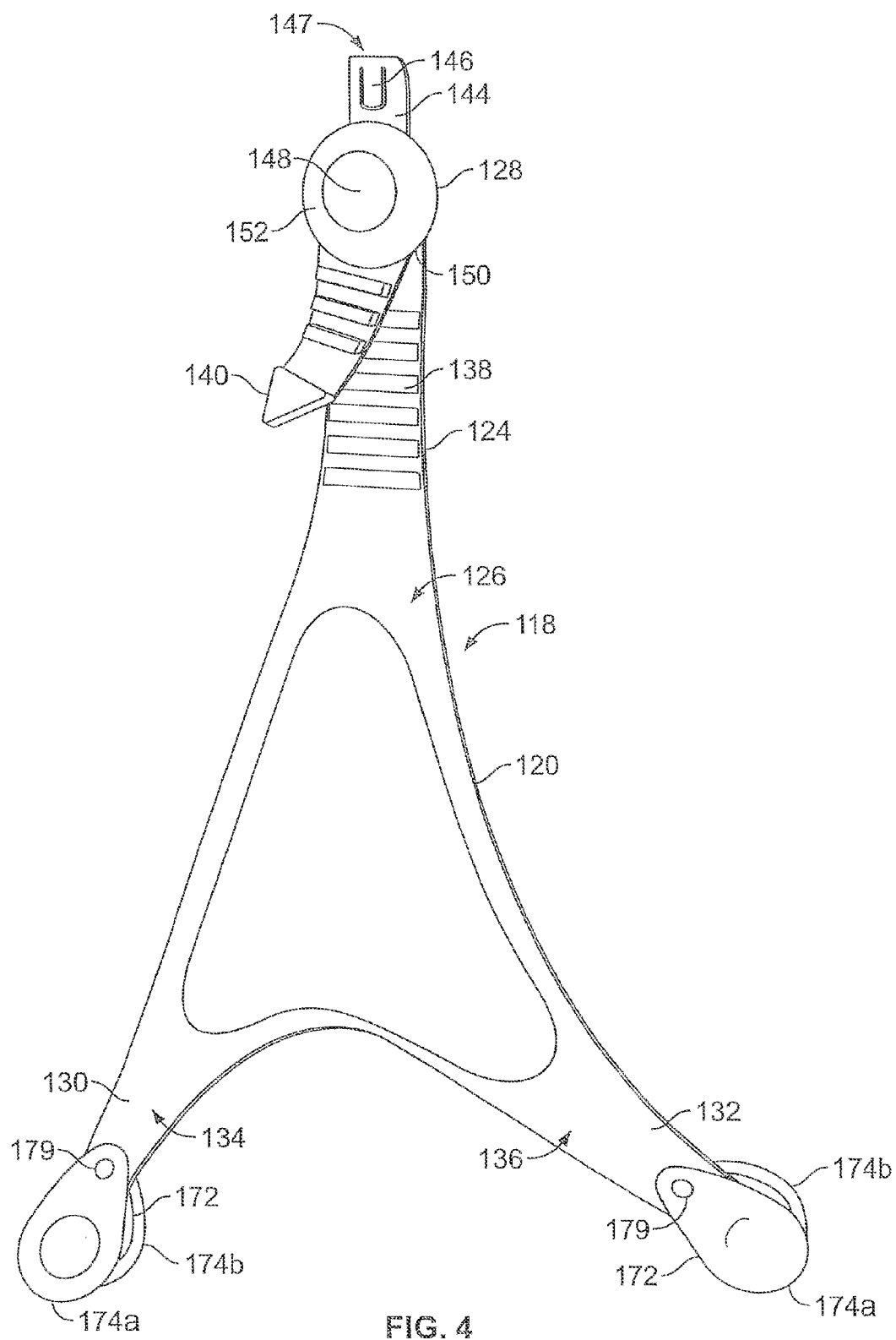
FIG. 4 shows a hands-free harness device according to another embodiment of the present invention.

Referring to FIG. 4, another embodiment of the breast shield harness 118 is shown according to a second preferred embodiment. The breast shield harness 118 includes a central harness body 120. The central harness body 120 does not include a body opening (see FIG. 1) but instead, includes an uninterrupted central panel that is sized and shaped to hold a breast shield in place. The breast shield adapted for use with this embodiment of the harness 118 may not have a funnel shaped part with a tubular (or cylindrical) extension, but instead, may preferably have a lower profile, such as a gently curved dome-like shape (not shown) in order to not protrude unduly from the mother, and may thusly be worn comfortably under a cover or other garment and held in place with the harness. Of course, the harness 118 could readily be adapted to overlie all of the underlying portions of the funnel-shaped breast pump previously described.

The central harness body panel 120 includes a top edge 126 from which a first strap 124 extends. The top edge 126 may again be merely an extension or portion of the body 120 as opposed to being connected via a seam or joint. Similarly, the central harness body 120 includes a first lower portion or corner 134 and a second lower portion or corner 136. The top edge 126, first and second corners 134, 136 are positioned to roughly define a triangular shape of the central harness body 120. It will be understood that other suitable shapes are contemplated by the invention. A second strap 130 extends from the first lower corner 134 and a third harness strap 132 extends from the second lower corner 136.

The first strap 124 includes, along its length, a plurality of grooves, which may be considered to define protrusions or teeth 138. Protrusions or grooved are considered to be equivalent, i.e., variations of elevation or thickness of the material to provide an alternating profile. The protrusions 138 (or grooves) permit the strap to be fixed in position with respect to a clip body, i.e., first clip 128, which is of the same or similar design as discussed above with a passageway 150 formed through the clip body 152 and a loop 144 and tab 146 arrangement forming a hanger or attaching element 147 extending from the clip body for attaching to a cooperating element (not shown) of a nursing brassiere (not shown). It will be understood that the exact design of the attaching element 147, like clip 128, itself, can be adapted to attach to different cooperating elements on nursing brassieres or to the shoulder strap without any separate element on the brassiere, as by providing different types of attaching elements, such as hooks, loops, buttons, snaps and other known devices. The clip body 152 includes a release button 148 for disengaging an internal ratchet element (not shown) from the grooves/teeth 138 when manipulated by a user.

The terminal end of strap 124 may include one or more gripping elements 140 sized and shaped to be grasped by the user. The gripping element 140 may function as a stop element, which is a thickened section of the strap 124 which resists being pulled through the passageway 150 of the clip body 152. In this manner, first clip 128 cannot be easily detached from the strap 124 by merely sliding off the end of the strap because the end 140 does not pass through the clip.

This embodiment, the straps 124, 130 and 132 and the harness body 120 are formed of an elastomeric silicone material. More preferably, the silicone material of the first strap 124 is of a relatively higher hardness than the remainder of the breast shield harness 118. In one example, the silicone material of the upper strap 124 may be of a durometer A hardness of about 60-80. In a preferred example, the silicone material of the upper strap 124 may be of a durometer A hardness of about 70. The straps 124, 130 and 132 may be formed in a unitary fashion with the harness body 120 or may be attached thereto by any suitable method, for example, use of heat or an adhesive. The material of the straps 130, 132 are preferably of a lesser hardness that of the upper strap 124, and in particular, may be of silicon material or the like, having a durometer A of about 20-40, and more preferably of about 30. The relatively harder material of the upper strap 124 provides a resistance to being pulled through the clip 128 and the relatively softer material of the lower straps 130, 132 permits the device 118 to self adjust, by stretching, to adapt to different sized and shaped breasts, for example, without increasing the overall tension or force exerted by the stretching of the device 118.

Figure 6:
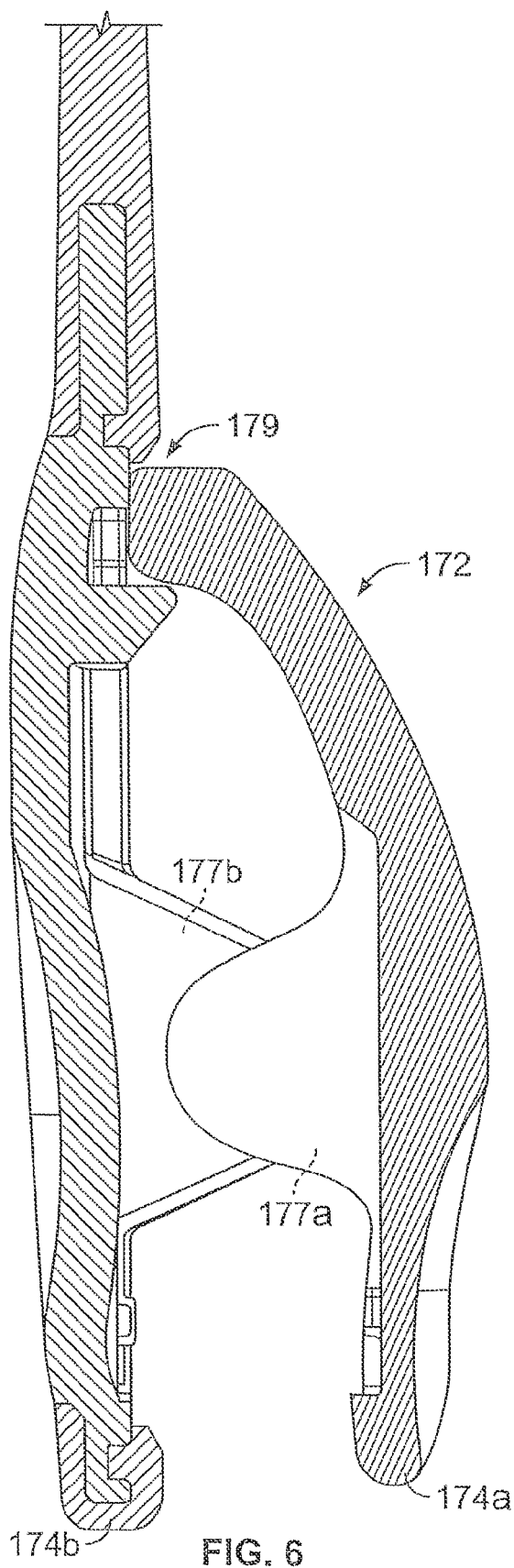
FIG. 6 is an enlarged sectional side view of a lower clip of FIG. 4.

Each of the second and third straps 130, 132 have at a terminal end thereof a clip 172 for attachment to a corresponding portion of a nursing brassiere or like garment (see FIG. 2). The clips 172 may be hooks or any suitable attaching device capable of grasping the material of or an area of the associated garment. In the embodiment shown in FIG. 4 and in more detail in FIG. 6, the clips 172 are spring-biased "alligator" type clips, which include a pair of opposed and toothed jaws 174A, 174B for grasping material therebetween. First jaw 174A is pivotally mounted to second jaw 174B by first extension 177A being pivotally mounted to second extension 177B, wherein extensions 177A, B are tab-shaped or arms which function to connect the first and second jaws at a mid-area thereof. An upper area of the clips 172 includes a clip/material fastener 179 for securing the clip to the material of the harness body (See FIG. 4). The fastener 179 may be a rivet or a pinch point of the clip or any suitable mechanism or method of securing the clip to the material of the body.

Figure 5:
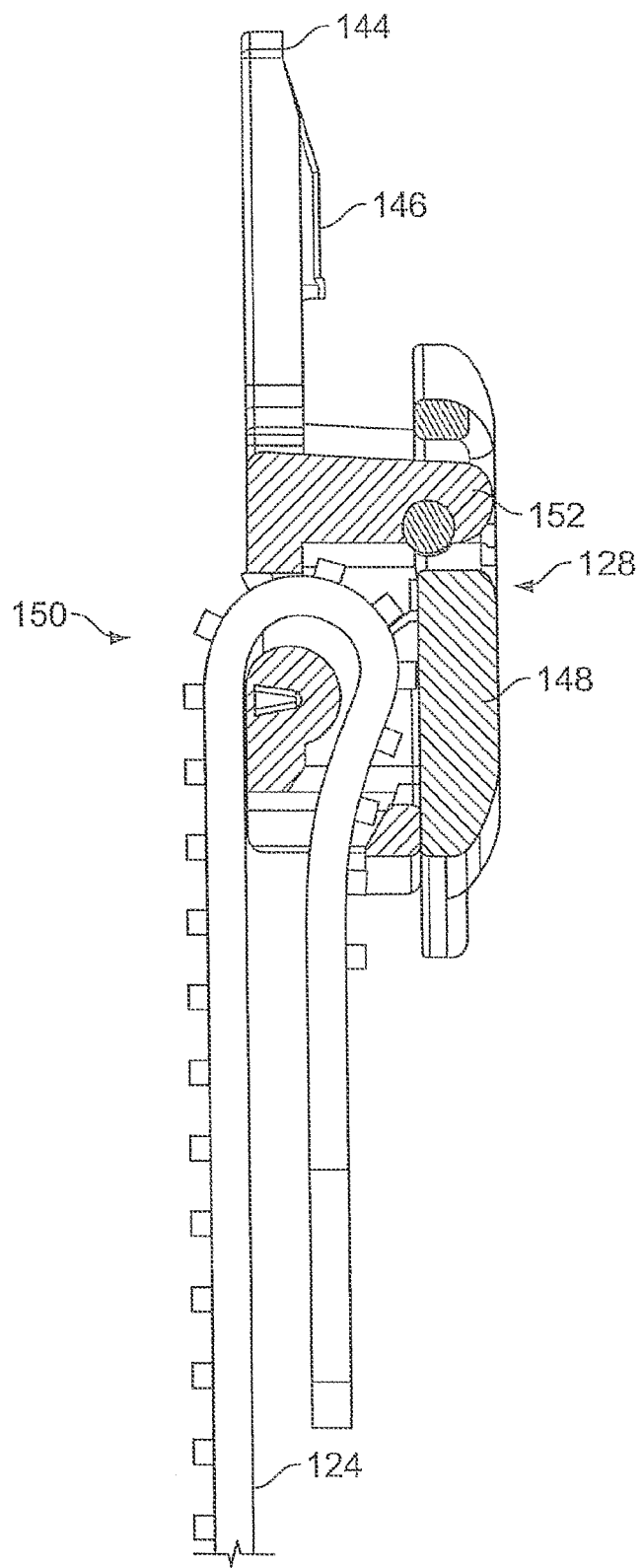
FIG. 5 is an enlarged sectional view of the upper clip along line 5-5 of FIG. 4.

FIG. 5 shows a sectional view of the upper clip 128 along line 5-5 of FIG. 4. The upper clip 128 includes a clip body 152 that includes a release tab or button 148 that is pivotally mounted to the clip body. A passageway 150 is defined between the clip body 152 and the tab 148 that is sized and shaped to receive the strap 124. Manipulation of the tab 148 to an open position permits the disengagement of the strap 124 in the clip 128 and permits the strap to be slid through the passageway 150 effectively shortening or lengthening the strap dependent upon the direction the strap is passed through the passageway. Additionally, the clip 128 and tab 148 act as a ratchet device when the tab 148 is in a closed position, permitting easy tightening of the strap 124 while preventing unwanted loosening. This allows for single-handed operation to tighten the strap.

Figure 7:
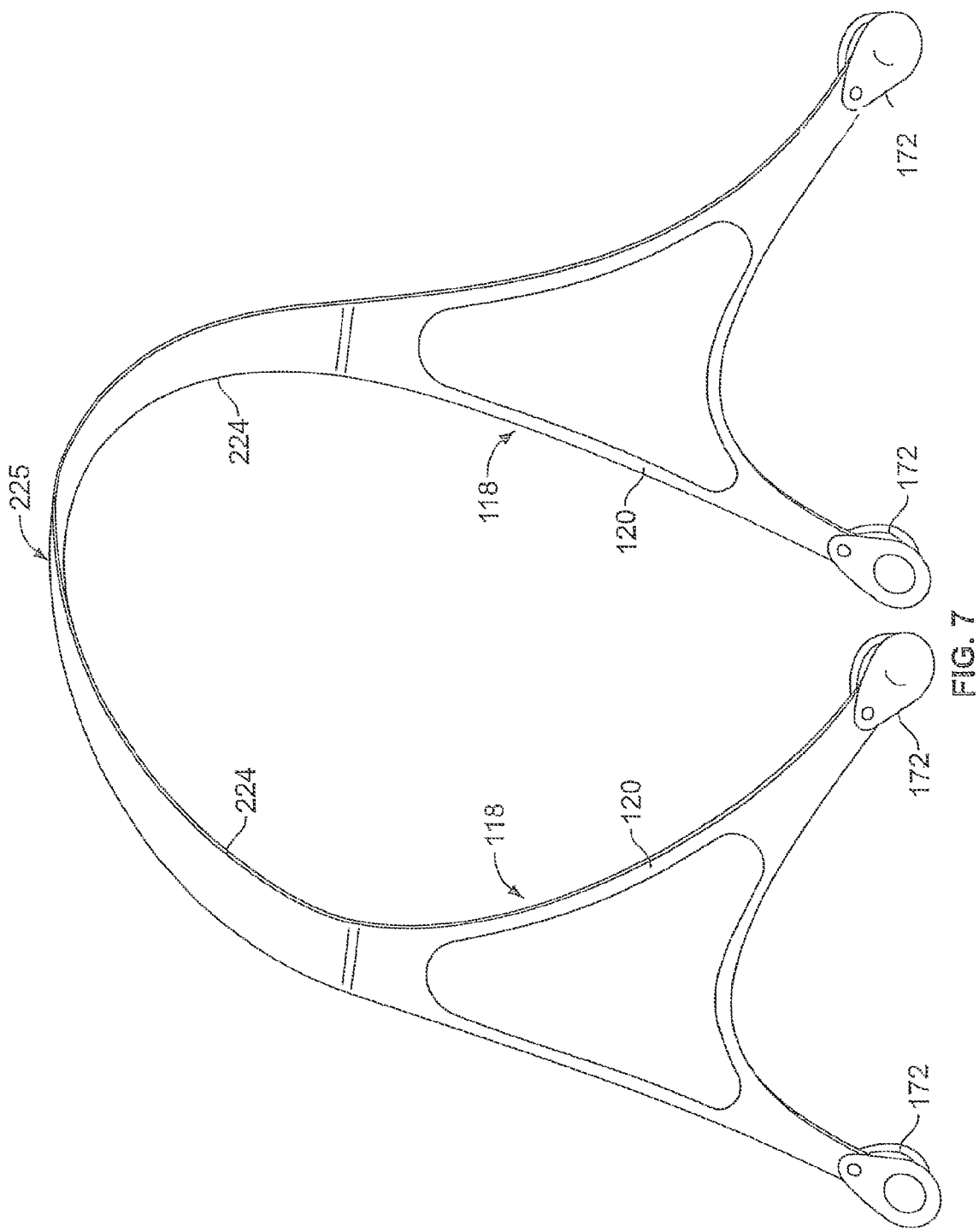
FIG. 7 is a perspective new of another embodiment of the invention using a neck strap.

FIG. 7 is a perspective new of another embodiment of the invention wherein a pair of breast shield harnesses 118 are provided and linked by a neck strap 224. Each of the breast shield harnesses 118 include one or more device for attaching to a garment at a lower point of the harness, for example, with a pair of clips 172 as described in more detail above (e.g. FIG. 6). Each central harness body 120 of each harness 118 includes an upper or first strap 224. The upper or first straps 224 are shaped and sized to pass behind the neck of the user and maintain the position of the harnesses 118 on the user. Preferably, the straps 224 include an adjustment mechanism 225, in this example a hook and loop feature, which permits the overall length of the combined straps 224 to be adjusted. Other mechanisms for permitting adjustment of the straps 224 are contemplated, such as, for example, snaps, sliding buckles, stretchable fabric, and so on. The strap 224 in some of these embodiments may be either in two parts or may be a single strap depending upon the mechanism employed for permitting adjustment or adaptation of the harness 118 to different sized or shaped users or other accommodations to different applications.

Figure 8:
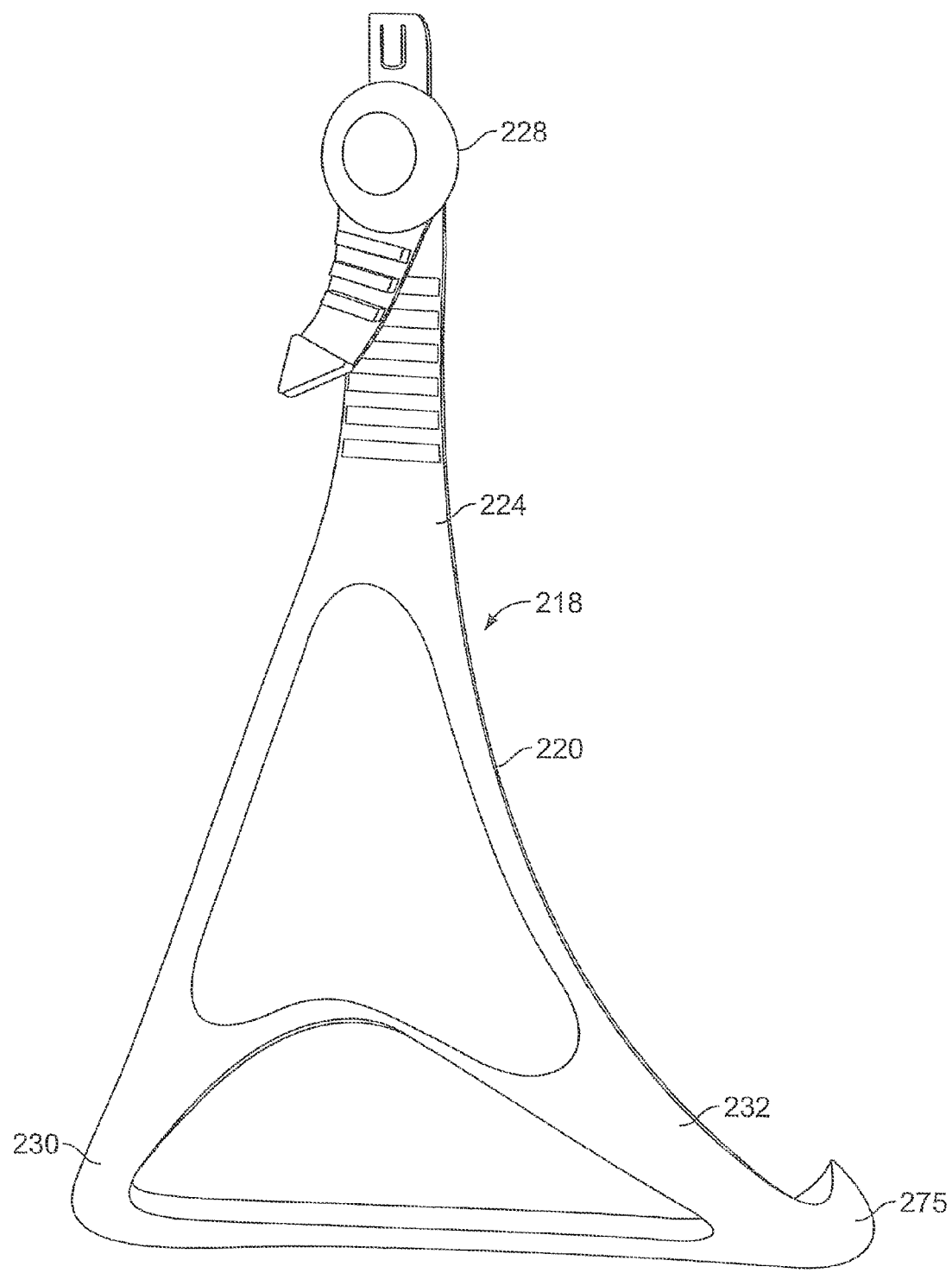
FIG. 8 is yet another embodiment of the invention.

FIG. 8 is yet another embodiment of the invention similar to design of the embodiment shown in FIG. 4 with another embodiment of an attaching mechanism 275 for attaching the bottom of the harness 318 to a nursing brassiere or like garment (not shown). The harness 318 includes a central harness body 320 with an upper or first strap 224. A first clip or upper clip 228 secures the strap 224 of the harness 318 to the garment. The central harness body 320 includes a pair of spaced harness straps 230 and 232 extending from lower points or areas of the central harness body 220. The span between straps 230 and 232 is occupied by a lower attachment member or hook 275 in the shape of a channel, extended hook or the like, which is sized and shaped to engage and releasably secure to part of the garment or nursing brassiere, such as an wire element, a fabric feature, a hem or edge or the like of the garment (See FIG. 2, for example).

It will thus be seen that the objects set forth above, among those made apparent from the preceding description, are efficiently attained and, since certain changes may be made in the above constructions without departing from the spirit and scope of the invention, it is intended that all matter contained in the above description or shown in the accompanying drawings shall be interpreted as illustrative and not in a limiting sense. It is also to be understood that the following claims are intended to cover all of the generic and specific features of the invention herein described and all statements of the scope of the invention that, as a matter of language, might be said to fall therebetween.

What is claimed is:

1. A breast pump breast shield harness device which is separate from and releasably attachable to a nursing garment for holding a breast pump breast shield to a breast for hands-free breast pumping, comprising:
   a breast pump breast shield harness body including a central panel, said central panel being sized and shaped to hold a breast shield;
   a first strap extending from a first position of said harness body;
   a first clip engaged with said first strap and having a fastening element for releasably connecting to an upper part of the nursing garment; and
   one or more secondary straps extending from said harness body, wherein each of said one or more secondary straps includes a second clip for engaging with a lower part of the nursing garment.

2. The device of claim 1, wherein said central panel is made of silicone rubber.

3. The device of claim 1, wherein said central panel includes a body opening formed therethrough, said body opening being sized and shaped to receive a portion of the breast shield therethrough and hold the breast shield in place.

4. The device of claim 3, wherein said body opening is sized and shaped to receive a cylindrical portion of the breast shield.

5. The device of claim 1, wherein said central panel is generally triangular in shape.

6. The device of claim 1, wherein said first strap extends from an upper portion of said harness body.

7. The device of claim 1, wherein said first strap is made at least in part of a stretchable material having a durometer A hardness of about 60 to about 80.

8. The device of claim 7, wherein said first strap is made of an elastic material having a durometer A hardness of in a range of about 60 to 80.

9. The device of claim 1, wherein said one or more secondary straps is made at least or in part of a stretchable material.

10. The device of claim 9, wherein said one or more or more secondary straps is made of an elastic material having a durometer A hardness in a range of about 30 to about 40.

11. The device of claim 10, wherein said first strap is made of a material having a greater hardness than the material of said one or more secondary straps.

12. The device of claim 1, wherein said first and secondary straps are made substantially entirely of an elastic material.

13. The device of claim 5 having two secondary straps extending from opposite sides of a lower portion of said harness body.

14. The device of claim 1, wherein each of said straps includes a clip device.

15. The device of claim 14, wherein said first strap includes a clip having a part through which said first strap is received to releasably and adjustably hold said first strap.

16. The device of claim 15, wherein said first clip is attachable to the nursing garment.

17. The device of claim 16, wherein said second clips further include a pair of opposed jaws biased to close and grip a portion of the nursing garment between said jaws.

18. A breast shield harness device which is separate from and releasably attachable to a nursing garment to hold a breast shield of a breast pump in place on a woman's breast, comprising:
    a harness body portion adapted to overlie the breast shield when the latter is positioned on a breast, said harness body portion having an upper part and a lower part;
    a first attachment device associated with said body upper part which releasably engages with an upper portion of the nursing garment above the breast;
    a second attachment device associated with said body lower part which releasably engages a lower portion of the nursing garment below the breast; and
    at least one of said attachment devices being adjustable toward and away from a central area of said harness body portion.

19. The device of claim 18, wherein said second attachment device has an elongated channel within which is received material forming the lower part of the nursing garment.

20. The device of claim 19, wherein said channel extends a distance substantially along an entire diameter of a cup of the nursing garment.

21. The device of claim 19, wherein the material of the nursing garment further includes an underwire which is received in said channel.

22. The device of claim 18, wherein said first attachment device has a part that is adapted to releasably attach to a standard element on the nursing garment used to affix an openable flap forming part of a brassiere cup in place, said harness body portion having a first elongated member extending from said upper body part which is received in another part of said first attachment device to releasably and adjustably hold said elongated member.

23. The device of claim 22, wherein said first elongated member is a strap having a toothed surface formed along at least a length thereof that is received in a ratchet mechanism forming said another part of said first attachment device.

24. The device of claim 18, wherein said first attachment device has a part that is adapted to releasably attach to a standard element on the nursing garment used to affix an openable flap forming part of a brassiere cup in place, said harness body portion having a first elongated member extending from said upper body part which is received in another part of said first attachment device to releasably and adjustably hold said elongated member.

25. The device of claim 24, wherein said second attachment device comprises two lower clips each having a pair of opposed jaws biased to close and grip a portion of the nursing garment between said jaws, said lower clips respectively being located on opposite sides of said lower body part.

26. The device of claim 25, wherein said harness body portion has second and third elongated members extending from respective sides of said lower body part, said lower clips being respectively located on said second and third elongated members.

27. The device of claim 26, wherein said first elongated member is a strap having a toothed surface formed along at least a length thereof that is received in a ratchet mechanism forming said another part of said first attachment device.

28. The device of claim 18, wherein said first attachment device engages with itself about a shoulder strap of the nursing garment.

29. The device of claim 28, wherein said second attachment device comprises two lower clips each having a pair of opposed jaws biased to close and grip a portion of the nursing garment between said jaws, said lower clips respectively being located on opposite sides of said lower body part.

30. A breast shield harness device which is separate from and releasably attachable to a nursing garment to hold a breast shield of a breast pump in place on a woman's breast, comprising:
    a pair of breast shield supports, each breast shield support having a harness body portion adapted to overlie the breast shield when the latter is positioned on a breast, said harness body portion having an upper part and a lower part;
    a first attachment device in the form of an elongated member extending between said upper parts of said breast shield body portions adapted to pass behind a user's neck;
    a second attachment device associated with said body lower part which releasably engages with a lower portion of the nursing garment below the breast; and
    at least one of said attachment devices being adjustable toward and away from a central area of at least one of said breast shield body portions.

31. The device of claim 30, wherein said second attachment device comprises two lower clips each having a pair of opposed jaws biased to close and grip a portion of the nursing garment between said jaws, said lower clips respectively being located on opposite sides of said lower body part.

32. The device of claim 17, wherein said harness body portion is made at least in part of an extensible material.

33. The device of claim 27, wherein said harness body portion is made at least in part of an extensible material.

34. The device of claim 31, wherein said harness body portion is made at least in part of an extensible material.

35. A breast shield harness device which is separate from and releasably attachable to a nursing garment to hold a breast shield of a breast pump in place on a woman's breast, comprising:
- a harness body portion adapted to overlie the breast shield when the latter is positioned on a breast; and
- means for releasably engaging said body portion to the nursing garment in a generally triangular three-point engagement.

* * * * *